(12) United States Patent
Heald et al.

(10) Patent No.: US 7,981,646 B2
(45) Date of Patent: Jul. 19, 2011

(54) PREPARATION OF VANILLIN FROM MICROBIAL TRANSFORMATION MEDIA BY EXTRACTION BY MEANS SUPERCRITICAL FLUIDS OR GASES

(75) Inventors: Steve Heald, Canterbury (GB); Steve Myers, Dartford (GB); Tim Walford, Surrey (GB); Keith Robbins, Surrey (GB); Colin Hill, Kent (GB)

(73) Assignee: SAF-ISIS, Souston (FR)

( * ) Notice: Subject to any disclaimer, the term of this patent is extended or adjusted under 35 U.S.C. 154(b) by 1123 days.

(21) Appl. No.: 10/550,945

(22) PCT Filed: Mar. 29, 2004
(Under 37 CFR 1.47)

(86) PCT No.: PCT/GB2004/001394
§ 371 (c)(1),
(2), (4) Date: Nov. 30, 2006

(87) PCT Pub. No.: WO2004/085663
PCT Pub. Date: Oct. 7, 2004

(65) Prior Publication Data
US 2007/0298475 A1    Dec. 27, 2007

(30) Foreign Application Priority Data
Mar. 28, 2003 (GB) .................................. 0307232.9

(51) Int. Cl.
*C12P 7/04* (2006.01)

(52) U.S. Cl. ...................................... 435/156; 435/252.1
(58) Field of Classification Search .................. None
See application file for complete search history.

(56) References Cited

U.S. PATENT DOCUMENTS

| 4,474,994 A | 10/1984 | Makin |
| 4,847,422 A | 7/1989 | Klemola et al. |
| 6,133,003 A | 10/2000 | Hopp et al. |
| 6,235,507 B1 * | 5/2001 | Muheim et al. ............... 435/147 |

FOREIGN PATENT DOCUMENTS

| EP | 0 885 968 | 12/1998 |
| WO | WO 00/50622 | 8/2000 |

* cited by examiner

*Primary Examiner* — Irene Marx
(74) *Attorney, Agent, or Firm* — Young & Thompson

(57) ABSTRACT

Crude solid vanillin-containing material is precipitated from a solution obtained by biotransformation, and purified by a process comprising contacting it with a purification fluid selected from (a) a liquefied gas whose pressure exceeds its critical pressure and whose temperature is below its critical temperature; (b) a supercritical fluid; (c) a gas. The fluid is preferably liquid carbon dioxide. The temperature is maintained below 25°. The product may be further purified by treatment with $CO_2$ in a fluid bed drier. The crude material is preferably one precipitated from a solution resulting from biotransformation of ferulic acid. A new strain of *Amycolatopsis* capable of generating high concentrations of vanillin with minimal odoriferous by-products (e.g. guaiacol) is also disclosed.

12 Claims, No Drawings

US 7,981,646 B2

PREPARATION OF VANILLIN FROM MICROBIAL TRANSFORMATION MEDIA BY EXTRACTION BY MEANS SUPERCRITICAL FLUIDS OR GASES

TECHNICAL FIELD

The present invention relates to methods and materials that may be used in the production of vanillin and to vanillin as produced using such methods and materials.

There is a demand for natural vanillin of high flavour quality. This requires the use of raw materials of natural origin, and that all process steps should be compatible with the requirements for natural flavours as recognised by the industry and regulatory authorities.

BACKGROUND ART

Vanilla is a flavouring material derived from the pods of the vanilla orchid. It has long been known to make vanilla extract by extracting vanilla pods with alcohol (ethanol). More recently, vanilla pods have been extracted with supercritical carbon dioxide, generally in conjunction with a co-solvent such as ethanol. Flavourant components dissolve in the carbon dioxide (and co-solvent), which is then separated from the solid (waste) material.

Because of the expense of vanilla pods, there have long been attempts to produce substitutes. The main constituent of vanilla flavour is vanillin (3-methoxy-4-hydroxybenzaldehyde). This has been produced from industrial waste materials such as sulphite waste liquors of the wood pulp industry. However it is not possible to make "natural grade" vanillin in this way, and such material is unacceptable to many.

It must be appreciated that the natural vanilla aroma and flavour originating in vanilla pods are due to a complex mixture of compounds, mostly phenolic, of which vanillin is merely the main one in terms of percentage composition. It generally constitutes something less than 3% by weight of vanilla pods. Someone seeking to produce "vanilla extract" from vanilla pods is not seeking to extract vanillin selectively, but to extract a mixture (which may be concentrated to produce a brownish oil). In contrast someone seeking pure vanillin would not consider vanilla pods as a starting material—they are far too expensive, with a low vanillin content—and the technology developed for preparing vanilla extracts would not be considered relevant.

It is known to convert ferulic acid into vanillin using various microorganisms. We have previously disclosed (WO 00/50622) that use of a special strain of *Pseudomonas putida* can lead to a culture medium containing 2.25 gl$^{-1}$ of vanillin, a molar yield of 75% based on ferulic acid consumed. Vanillin was recovered by separating the culture broth from the cells and extracting it with an organic solvent (butyl acetate).

Haarman & Reimer GmbH have disclosed (U.S. Pat. No. 6,133,003) two strains of *Amycolatopsis*. Using one of them they achieved a culture medium containing up to 11.5 gl$^{-1}$ of vanillin and 1 gl$^{-1}$ of unreacted ferulic acid. These concentrations were determined by HPLC. There is no disclosure of any work-up technique or the isolation of the product.

Givaudan-Roure (International) S.A. have disclosed (EP-A-0885968) the use of *Streptomyces setonii* to produce "vanillin and several by-products". The concentration of vanillin is said to be 8-16 gl$^{-1}$, though in the actual examples it ranges from 3.10 to 13.9 gl$^{-1}$, in the latter case accompanied by 0.4 gl$^{-1}$ of guaiacol. The co-production of guaiacol is represented as being advantageous. The products are extracted by solvent extraction using methyl tert-butyl ether.

In many fields, the use of organic solvents is now seen as undesirable. This is certainly the case in the production of food-grade materials, especially if they are to be of "organic" quality.

SUMMARY OF THE INVENTION

We have now developed a process for the production of vanillin which does not require the use of organic solvents. In a first aspect the invention provides:

a method of purifying a crude solid vanillin-containing first material comprising:

(a) purifying said first material by a process comprising contacting it with a purification fluid selected from (a) a liquefied gas whose pressure exceeds its critical pressure and whose temperature is below its critical temperature; (b) a supercritical fluid; (c) a gas; to provide a solid vanillin-containing second material which is purer-than said first material in terms of its vanillin content.

The first solid material is preferably produced by (i) a step of carrying out a biotransformation process to generate a biotransformation medium which contains vanillin produced by said biotransformation process; and (ii) a step of precipitating a crude first solid vanillin-containing solid material from a solution which is or is derived from said biotransformation medium.

Desirably at all times the vanillin-containing materials are maintained at temperatures not exceeding 25° and preferably not exceeding 10°.

Preferably the purification involves the dissolution of the vanillin in the purification fluid, and its separation from undissolved impurities.

Alternatively or additionally, the method involves treating solid vanillin-containing material with a gas (preferably $CO_2$) in a fluidised bed, which carries away impurities and leaves behind purified solid vanillin material.

The crude first material may be obtained by precipitation from a solution, preferably in a crystalline or microcrystalline state. The solution may be a biotransformation medium, or may be derived from such a medium, e.g. by one or more steps such as removal of biocatalyst (which may be whole cells, cell parts, or immobilised enzyme), pasteurisation and concentration.

The biotransformation medium is generally from a biotransformation process which produces vanillin, usually by the biotransformation of ferulic acid into vanillin.

The ferulic acid is preferably derived from a natural plant source, particularly a food plant source, e.g. rice, maize, sugar beet, wheat or turmeric (*Curcuma longo*), generally waste material such as bran.

Preferably the biotransformation medium is a culture medium, preferably containing *Actinomycetales* microorganisms such as *Streptomyces setonii* or *Amycolatopsis* organisms, most preferably of the strain deposited under accession number IMI390106 or mutants thereof which are (a) resistant to spectinomycin and (b) capable of producing vanillin substantially free from guaiacol. Preferably the organism is able to produce a medium containing at least 5 g/l and preferably at least 10 g/l of vanillin, preferably substantially free from odoriferous by-products. Thus it is desirably possible to obtain a crude solid vanillin-containing material which contains not more than 100 ppm of guaiacol.

In another aspect the invention provides solid vanillin material having the following characteristics:

(i) absence of solvent residues;
(ii) absence of off-odours;
(iii) colour: white;

(iv) isotope ratio consistent with production from a precursor derived from a natural plant source. Preferably none of guaiacol, vinyl guaiacol, eugenol and isoeugenol is present at more than 100 ppm.

In another aspect the invention provides organisms of the strain deposited under accession number IMI390106 or mutants thereof which are (a) resistant to spectinomycin and (b) capable of producing vanillin substantially free from guaiacol.

DETAILED DESCRIPTION OF THE INVENTION a) Novel Microorganism

Zyl 926 is a new organism which the present inventors have produced. It has been deposited on Mar. 2, 2003 with CABI Bioscience, Egham TW20 9TY, GB and given the accession number IMI 390106. It has been identified as a strain of *Amycolatopsis*. It has the following characteristics:—

(i) Resistance to spectinomycin (determined by plating strains onto ISPII agar (see below) containing 1 g/l spectinomycin, incubating, and observing the growth or non/growth of colonies);

(ii) Morphology:

| | |
|---|---|
| Media: | ISPII medium, 5 day evaluation |
| Form: | Irregular |
| Elevation: | Raised |
| Margin: | Curled/undulate |
| Colony Colour: | Yellow/beige |
| Spore Colour: | White |
| Surface: | Dull, presporulation |

The criteria for selection of the strain were that it be:—
Genetically stable.
Safe (Class 1).
Easy to grow to high biomass concentrations using a cheap carbon source.
Produce concentrations of vanillin significantly higher than existing strains.
Convert nearly all the ferulic acid supplied.
Carry out the conversion in an acceptable time period.
Produce no significant off-flavour by-products, or by-products that colour the product.

b) Microbiological Process

An organism having a known antibiotic resistance (preferably Zyl 926) is incubated in the presence of the antibiotic to prepare a stock of the organism, essentially free of other organisms. Subsequent processes use this stock material, without added antibiotic.

A sterile medium is inoculated with the organism, which is cultured. Ferulic acid is added to the cultured organism, and undergoes bioconversion to vanillin. The broth, containing the vanillin in solution, is removed and clarified.

c) Downstream Purification

An aqueous solution of vanillin (generally the clarified broth from (b)) is treated (typically by concentration and cooling) to cause solid vanillin to separate. This is collected and purified, preferably by selective extraction into a purification fluid, preferably $CO_2$, preferably in a liquid state though a supercritical fluid such as $CO_2$ may be used. The liquid is preferably at a pressure greater-than the critical pressure (e.g. at least twice the critical pressure) and at a temperature below the critical temperature (e.g. at least 10° below). Using $CO_2$, we favour pressures around 200 bar (about 3 times Pc which is 74 bar) and temperatures between the freezing point and Tc (31°), preferably at least 10° below Tc. Other possible fluids include nitrous oxide, ethylene and Freons, such as Freon 13.

Extraction with carbon dioxide is favoured because of its good selectivity, ability to deal with variations in feedstock, operation at low temperature and good solvating power. Extraction efficiencies of 95% have been achieved to yield a product with a vanillin content of 98-100%. This product may be milled to aid rapid dissolution in formulation applications. The resulting material may be further purified by fluidised bed "drying" to remove volatile impurities. Indeed this could be used for the primary purification of the separated solid vanillin.

This form of purification, involving the direct production of solid crude vanillin, requires a starting solution which contains predominantly vanillin, with only small amounts of impurities and unreacted ferulic acid. In particular, odoriferous contaminants (such as guaiacol) are very undesirable. Desirably the concentration of vanillin in a broth from a microbiological process should be at least 5 $gl^{-1}$ and preferably at least 10 $gl^{-1}$. The broth obtained from process (b) using Zyl 926 is particularly suitable.

(d) Natural/Organic Vanillin

The vanillin which can be produced can meet the following criteria:

(i) Vanillin content of $\geq 98\%$ w/w.

(ii) No odorous impurity (off-aroma) such as guaiacol, vinylguaiacol, eugenol, isoeugenol present at more than ca 100 ppm in the solid vanillin product.

(iii) Colour. An 'L' value of $\geq 94$ determined using a Minolta chromameter calibrated with propylene glycol and using samples of 6% vanillin in propylene glycol.

(iv) Isotope ratios consistent with the ferulic acid precursor having been entirely derived from a natural plant source (e.g. maize, sugar beet or rice) as defined by authorities such as the French Ministere de L'Economie des Finances et de L'Industrie (59, Bd Vincent Auriol, 75703, Paris, Cedex 13, France).

Some embodiments of the invention will now be described in greater detail by way of example.

1. Preparation of Stock Inoculum

ISPVII agar, containing 10 g/L malt extract, 4 $gl^{-1}$ yeast extract, 4 $gl^{-1}$ glucose and 20 $gl^{-1}$ agar, was adjusted to pH 7.4, and 1 $gl^{-1}$ spectinomycin was added as the agar cooled (and before it gelled). Petri dishes containing the sterile ISP II agar were inoculated aseptically with Zyl 926 culture. These petri dishes were incubated for a minimum of 72 hours at 30° C. to generate colonies across the plates.

Single colonies were lifted from the agar and used to inoculate 50 ml portions of sterile SFG medium containing 1 $gl^{-1}$ spectinomycin in 250 ml Erlenmeyer flasks. The antibiotic was added by sterile filtration. (SFG medium:per liter of water Soya flour (Nutrisoy) 5 g; di-potassium hydrogen orthophosphate 1 g; magnesium sulphate heptahydrate 1.64 g; glycerol 20 g). Flasks were incubated at 30° C. and 200 rpm for 3 to 5 days in a shaking incubator.

After visual assessment of satisfactory luxuriant growth an equal volume of sterile cryopreservative was added: 20% glycerol/10% lactose solution in water.

The resulting suspension of cells was then dispensed into sterile vials in appropriate aliquots for inoculation of subsequent stages. Culture stock was preserved by storage at −80° C.

2. Fermentation 0.7 ml of culture (thawed) prepared as above was used to inoculate 1 liter of sterile SFG medium in a 1.25l fermenter, configured with two 6 bladed Rushton impellers and static air sparger.

The fermenter was cultured at 37° C. and 100 rpm with an airflow of 1.7l min$^{-1}$ (1.7vvm) at pH 7.2 for 48 hours prior to using this primary seed stage to inoculate 40l of sterile SFG medium (7 gl$^{-1}$ glycerol).

This stage was cultured at 41° C. and 55 rpm (two Rushton turbines in a 50l fermenter) for 43 hours at an airflow of 40l min$^{-1}$.

Two liter portions of this culture were used to inoculate 38l of a sterile SFG medium in a 50l fermenter. This stage was cultured at 41° C. and 20l min$^{-1}$ airflow with control of dissolved oxygen at 70% of saturation by cascade control of agitator speed.

After 13 hours of incubation the pH in each fermenter was adjusted over the course of 60 minutes to 8.5 by addition of 2M sodium hydroxide. Substrate (ferulic acid) was added as a single charge, dissolved in 10l of 0.5M sodium hydroxide at 41° C., with adjustment of this solution to pH 8.5 with 10M base. The correct concentration was verified by HPLC analysis, as was the subsequent course of reaction. Culture conditions were maintained as above.

Reaction of substrate to product was complete after between 40 and 51 hours.

The amounts of ferulic acid were varied, and the strength of the SFG final stage medium was adjusted according to substrate concentration:

| Substrate concentration (gl$^{-1}$) | Soyflour (Nutrisoy) (gl$^{-1}$) | di-Potassium hydrogen orthophosphate (gl$^{-1}$) | Magnesium Sulphate heptahydrate (gl$^{-1}$) | Polypropylene glycol (ml) | Glycerol (gl$^{-1}$) |
|---|---|---|---|---|---|
| 18 | 5 | 1 | 1.64 | 0.2 | 7 |
| 25 | 8.6 | 1.7 | 2.8 | .35 | 12 |
| 32 | 8.6 | 1.7 | 2.8 | .35 | 12 |

3. Downstream Purification

Extraction: At the conclusion of the biotransformation, the pH of the broth was adjusted to 6.7+/−0.1. It was then heat treated at 55° C. for 5 minutes and then cooled to 30° C. Heat treated broth, 50l was then clarified either by centrifugation at −11,000×g or more preferably by filtration using a filter aid, e.g. Celite 512. The filter press used for clarification, a British Filters PA20M, is pre-coated with 10 g of Celite per plate and 12 gl$^{-1}$ of bodyfeed or admix added to the broth. The resulting filtrate was then ultrafiltered through any suitable membrane, preferably one made of polysulphone and having a molecular weight cut-off of 10,000 Daltons.

To maximise recovery the ultrafiltrate retentate, 4l, was diafiltered three times with an equal volume of water.

The combined ultrafiltrate and diafiltrate, 66l, were then adjusted to pH 6.6+/−0.1 and concentrated to approximately 50 gl$^{-1}$ vanillin under reduced pressure using a pot still. The concentrate temperature was maintained between 20 and 35° C. at a vacuum of 1.3 to 26 KPa. On subsequent cooling of the final concentrate to 5-10° C. in a suitable jacketed vessel, a crude vanillin product precipitated. After cooling at 5-10° C. for not less than 3 hours the crude product was recovered by any suitable means, but preferably filtration using a basket centrifuge (Broadbent 9 inch type 41) and dried in trays at 30-40° C. and 80 KPa.

Alternatively, the clarified broth may be concentrated to approximately 40 gl$^{-1}$ at a higher temperature suitably 30-35° C., and the resulting concentrate, after adjustment of pH to 5.9, extracted with an equal volume of n-butyl acetate. After separation of the phases the rich solvent extract is concentrated to 320 gl$^{-1}$ vanillin using a pot still and cooled, whereupon a precipitate of crude vanillin is formed which is recovered by vacuum filtration on a Nutsche filter. The filter cake can then be washed with 2 volumes of hexane to remove the n-butyl acetate and then dried in trays under vacuum, 80 KPa and 40° C.

The resulting dry material may be purified by either of the methods outlined under Purification below.

Purification

Dried product (554 g, 53% vanillin) from initial downstream processing was charged into an extraction vessel of a carbon dioxide extraction rig. Pressure was raised to 20 MPa and temperature set at 5° C. Liquid carbon dioxide rich in vanillin was piped to the evaporator, maintaining the above temperature and pressure conditions. In the evaporator the pressure was reduced to approximately 3 MPa whereupon white crystals of vanillin precipitated. Temperature was maintained in the evaporator by circulation of a heat transfer medium in the evaporator jacket at 70° C. Vanillin (278.9 g 95% yield) was recovered from the evaporator.

The purified material may be further purified in a fluidised-bed dryer. This example used one produced by Sherwood Scientific, Cambridge, GB. Treatment at 55° C. for 2 hours with a flow rate of $CO_2$ of 14.8-15.3L/sec caused the organoleptic quality to be greatly improved by a method that is simple to use, acceptable as regards 'natural' and 'organic' specifications for flavours, and entails only minor (1-2%) losses consistent with normal handling operation losses. The colour of the product was determined using a Minolta chromameter as explained above. It has an 'L' value of 99.5; and also an 'a' value (red-green hue) of 0.01, and a 'b' value (yellow-blue hue) of 2.84.

Fluidisation with air is also possible, but less preferred than $CO_2$.

Fluidised bed treatment may also be used instead of the liquid $CO_2$ extraction method for the initial purification.

Results of some runs are presented in Table 1 below:

TABLE 1

| Production of vanillin using Zyl 926 | | | |
|---|---|---|---|
| Ferulic acid added | 18 | 25 | 31-33 |
| Conc. of vanillin formed (g/l) | 10.8 | 13.8 | 17.95 |
| Fermentation Time (h) | 38.7 | 51.5 | 50.5 |
| Residual Ferulic acid cons (g/l) | 0.49 | 1.01 | 1.52 |
| Volumetric Productivity (gV/L/H) | 0.279 | 0.268 | 0.347 |

TABLE 1-continued

| Production of vanillin using Zyl 926 | | | |
|---|---|---|---|
| Yields of vanillin on ferulic acid supplied (% g/g) [% of theoretical yield] | 62.17 [79.7%] | 55.9 [71.7%] | 56.17 [62.9%] |

The invention claimed is:

1. A method of preparing vanillin which comprises:
(i) carrying out a biotransformation process which comprises the biotransformation of ferulic acid in the presence of a microorganism consisting of *Amycolatopsis* sp. IMI 390106 , to generate a biotransformation medium which contains vanillin produced by said biotransformation process and substantially free from odoriferous by-products;
(ii) precipitating a crude vanillin product from a solution which is or is derived from said biotransformation medium; and
(iii) purifying said vanillin product by a process comprising contacting the vanillin product with a purification fluid selected from (a) a liquefied gas whose pressure exceeds its critical pressure and whose temperature is below its critical temperature; (b) a supercritical fluid; (c) a gas; to provide solid vanillin.

2. A method according to claim 1 wherein said purification fluid is a liquefied gas.

3. A method according to claim 1 wherein said purification fluid is at a temperature below 25°.

4. A method according to claim 1 wherein said purification fluid is (a) a liquefied gas or (b) a supercritical fluid.

5. A method according to claim 1 wherein said fluid is carbon dioxide.

6. A method according to claim 1 including a further step (iv) of treating said vanillin of step (iii) with a gas in a fluidized bed.

7. A method according to claim 1 in which the supercritical fluid and/or the gas is carbon dioxide.

8. A method according to claim 1 in which the ferulic acid is derived from a natural plant source.

9. A method according to claim 1 in which the biotransformation medium is a culture medium.

10. A method according to claim 1, wherein said *Amycolatopsis* sp. IMI 390106 is capable of producing vanillin substantially free from guaiacol.

11. A method according to claim 1, wherein said *Amycolatopsis* sp. IMI 390106 is capable of producing vanillin containing not more than 100ppm of guaiacol.

12. A method according to claim 1 wherein said solid vanillin obtained at step (iii) has a vanillin content of 98% to 100%.

* * * * *